United States Patent [19]

Ilsink

[11] Patent Number: Plant 5,648

[45] Date of Patent: Jan. 28, 1986

[54] ROSE PLANT INTERVAL

[75] Inventor: G. Peter Ilsink, Leersum, Netherlands

[73] Assignee: Jackson & Perkins Company, Medford, Oreg.

[21] Appl. No.: 626,160

[22] Filed: Jun. 29, 1984

[51] Int. Cl.[4] ..... A01H 5/00

[52] U.S. Cl. ..... Plt./23

[58] Field of Search ..... Plt./23

*Primary Examiner*—Robert E. Bagwill

*Attorney, Agent, or Firm*—Manford R. Haxton

[57] ABSTRACT

A new and distinct variety of rose plant of the floribunda class, having the unique combination of its vigorous plant, producing long stems bearing stiff petaled, near white buds, opening to near white fragrant blooms; its mildew resistance.

1 Drawing Figure

1

This present invention relates to a new and distinct variety of rose plant of the floribunda class which was originated by crossing an unnamed variety with the variety Golden Times, U.S. Plant Pat. No. 4,044.

The primary object of this breeding was to produce a new rose variety suitable for use as a greenhouse grown cut flower source having the long vase life characteristic of Golden Times, but of a different color. This objective was substantially achieved along with other desirable improvements as evidenced by the following unique combination of characteristics which are outstanding in the new variety and which distinguish it from its parents as well as from all other varieties of which I am aware:

1. A vigorous plant producing flowers on long stems in greenhouse culture;
2. Buds near white, with green tints, edged when young with red;
3. Open flowers near white with pink tints and yellowish center;
4. Stiff petals;
5. Moderate fragrance;
6. Good resistance to Rose powdery mildew.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color in terminology in accordance with The Royal Horticultural Society Colour Chart except where ordinary dictionary significance of color is indicated:

Parentage:

*Seed parent.*—Unnamed variety.

*Pollen parent.*—Golden Times, U.S. Plant Pat. No. 4,044.

Classification:

*Botanical.*—Rosa hybrid.

*Commercial.*—Floribunda.

2

FLOWER

Observations made from specimens grown in a greenhouse at Irvine, Calif. in May.

Blooming habit: Continuous.

Bud:

*Size.*—1" when petals start to unfurl.

*Form.*—Long, urn-shaped.

*Color.*—When sepals first divide, yellow-green 145D, petal tips edged with Red 53C. Color becomes near white with edging much smaller and lighter before sepals fold out. When half blown; upper side of petals near white, center of flower being near Orange 27C; lower side of petals near white.

*Sepals.*—Color: Green 138B. Surface texture: Slightly pubescent. Three appendaged sepals lightly appendaged. Two appendaged sepals hairy edged.

*Receptacle.*—Color: Green 138B. Shape: Funnel. Size: Very small. Surface: Hairy.

*Peduncle.*—Length: Short. Surface: Smooth, with very fine pubescence. Color: Green 138B. Strength: Stiff, erect.

*Opening.*—Very slowly, spiral.

Open bloom:

*Size.*—Large. Average open size 3¾".

*Borne.*—Singly, or several together, in clusters.

*Stems.*—Long to medium, strong.

*Form.*—When first open, high center. Permanence: Flattens, outer petal edges slightly curled.

*Petalage.*—Number of petals under normal conditions: 25–30.

*Color.*—Center of flower: Upper side of petals — Near white, with tint of Orange 27C, center showing much yellow near 9B. Reverse side of petals, near white. Base of petals near white. Major color: In common terminology, flower color is ivory, close to R.H.S. Orange 27D.

*Variegations.*—None.

*Discoloration.*—General tonality at end of first day: Orange 27D. Third day: Orange 27D.

*Fragrance.*—Moderate.

Petals:

*Texture.*—Thick.

*Shape.*—Round.

*Form.*—Tips slightly recurved.

*Arrangement.*—Imbricated. Petaloids in center, few, large.

*Persistence.*—Hang on and dry.

*Lastingness.*—On the plant, very long. As cut flower, very long.

Reproductive parts:

*Anthers.*—Small, many. Color: Yellow. Arrangement: Regular around styles.

*Filaments.*—Color: Yellow green 154B.

*Pollen.*—Lemon yellow.

*Stigmas.*—Color: White, at base Red 51A on distal half.

PLANT

Form: Bush.

Growth: Very vigorous, upright.

Foliage: Number of leaflets on normal mid-stem leaves: Usually 7, sometimes 5.

*Size.*—Large.

*Quantity.*—Normal.

*Color.*—New foliage: Normal green with very little reddish overlay. Old foliage: Normal green, close to 139A, on upper side; lighter, near 129C, on lower side.

Leaflets:

*Shape.*—Broadly oval.

*Texture.*—Leathery.

*Edge.*—Serrated, slightly undulated.

*Serration.*—Single, small.

*Petiole.*—Rachis: Color: Green. Underside: With prickles.

*Stipules.*—Long, bearded.

*Disease resistance.*—Resistant to mildew, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Long, straight.

*Color when young.*—Green.

Small prickles:

*Quantity.*—On main stalks, none. On laterals, none.

I claim:

1. A new and distinct variety of rose plant of the floribunda class, substantially as herein shown and described, characterized particularly as to novelty by the unique combination of its vigorous plant, producing long stems bearing stiff petaled, near white buds, opening to near white fragrant blooms; its mildew resistance.

* * * * *

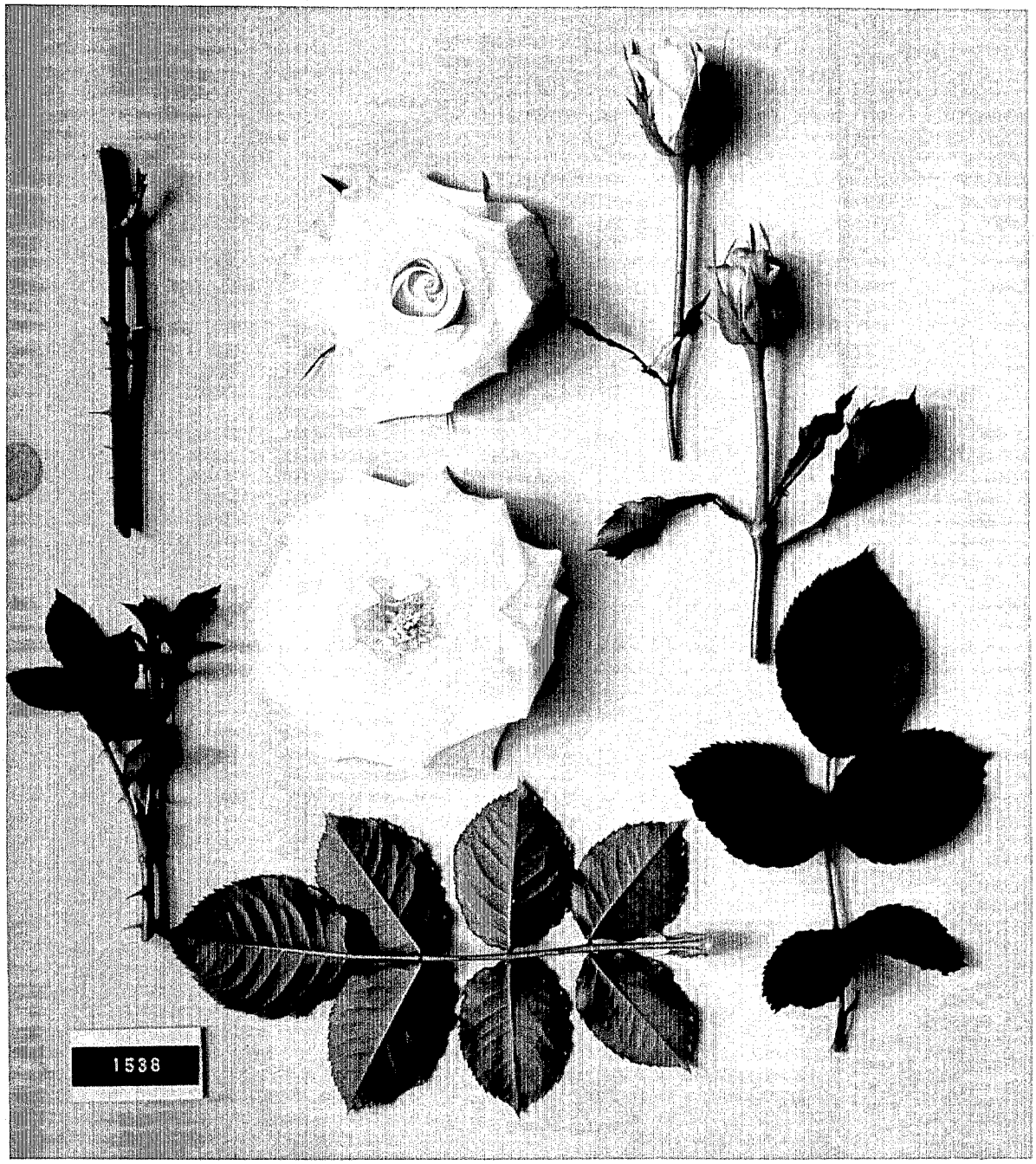
1538